(12) United States Patent
Abbas et al.

(10) Patent No.: US 7,368,138 B2
(45) Date of Patent: May 6, 2008

(54) EXTRACTION OF PHYTOSTEROLS FROM CORN FIBER USING GREEN SOLVENTS

(75) Inventors: Charles Abbas, Champaign, IL (US); Anne M. Rammelsberg, Decatur, IL (US); Kyle Beery, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 292 days.

(21) Appl. No.: 10/392,926

(22) Filed: Mar. 21, 2003

(65) Prior Publication Data

US 2003/0235633 A1 Dec. 25, 2003

Related U.S. Application Data

(60) Provisional application No. 60/365,816, filed on Mar. 21, 2002.

(51) Int. Cl.
*A01N 65/00* (2006.01)
*C07D 303/12* (2006.01)

(52) U.S. Cl. ................... 424/750; 552/545
(58) Field of Classification Search ............. 424/750; 514/169; 552/545; 44/308
See application file for complete search history.

(56) References Cited

U.S. PATENT DOCUMENTS

| | | | |
|---|---|---|---|
| 3,691,211 A * | 9/1972 | Julian | |
| 4,038,481 A | 7/1977 | Antrim et al. | |
| 4,104,463 A * | 8/1978 | Antrim et al. | |
| 4,242,502 A | 12/1980 | Malinow et al. | |
| 4,420,427 A | 12/1983 | Hamunen | |
| 5,023,249 A | 6/1991 | Kondo et al. | |
| 5,117,016 A * | 5/1992 | Tackett et al. | |
| 5,770,749 A | 6/1998 | Kutney et al. | |
| 5,843,499 A | 12/1998 | Moreau et al. | |
| 5,929,062 A * | 7/1999 | Haines | |
| 5,932,562 A | 8/1999 | Ostlund, Jr. | |
| 6,031,118 A | 2/2000 | van Amerongen et al. | |
| 6,063,776 A | 5/2000 | Ostlund, Jr. | |
| 6,087,353 A | 7/2000 | Stewart et al. | |
| 6,162,483 A | 12/2000 | Wester | |
| 6,171,638 B1 | 1/2001 | Gugger et al. | |
| 6,197,357 B1 * | 3/2001 | Lawton et al. | |
| 6,352,845 B1 | 3/2002 | Buchanan et al. | |
| 6,441,206 B1 | 8/2002 | Mikkonen et al. | |
| 6,589,588 B1 | 7/2003 | Wester et al. | |
| 6,623,780 B1 | 9/2003 | Stevens et al. | |
| 2002/0107232 A1 | 8/2002 | Flickinger et al. | |
| 2003/0003131 A1 | 1/2003 | Dyer et al. | |

FOREIGN PATENT DOCUMENTS

| GB | 1081667 | 8/1967 |
|---|---|---|
| WO | WO 99/56558 A1 | 11/1999 |
| WO | WO 00/52029 A1 | 9/2000 |
| WO | WO 00/61694 A1 | 10/2000 |
| WO | WO 00/69280 A2 | 11/2000 |
| WO | WO 01/37681 A1 | 5/2001 |
| WO | WO 02/28204 A1 | 4/2002 |

OTHER PUBLICATIONS

Co-pending U.S. Appl. No. 09/444,713, "Phytosterol and Phytostanol Compositions," inventor Gottemoller, T.V., filed Nov. 24, 1999, not published.
Co-pending U.S. Appl. No. 10/410,193, "Hydrothermically Processed Compositions Containing Phytosterols," inventors Binder et al., filed Apr. 10, 2003, not published.
Co-pending U.S. Appl. No. 10/428,067, "Coated, Agglomerated Phytochemicals," inventors Kuellmer et al., filed May 2, 2003, not published.
Hanmoungjai, P., et al., "Enzymatic Process for Extracting Oil and Protein from Rice Bran," *J. Am. Oil Chem. Soc.* 78:817-821, AOCS Press (Aug. 2001).
Moreau, R.A., et al., "Phytosterols in the aleurone layer of corn kernels," *Biochemical Soc. Trans.* 28:803-806, Biochemical Society (2000).
Moreau, R.A., et al., "Comparison of Oil and Phytosterol Levels in Germplasm Accessions of Corn, Teosinte, and Job's Tears," *J. Agric. Food Chem.* 49:3793-3795, American Chemical Society (Jul. 2001).
Moreau, R.A., et al., "Diferuloylputrescine and *p*-Coumaroyl-feruloylputrescine, Abundant Polyamine Conjugates in Lipid Extracts of Maize Kernels," *Lipids* 36:839-844, AOCS Press (Aug. 2001).
"New Processes for Generating Valuable Co-Products From Corn Fiber, Progress Reports Jan. 1996-Sep. 1996, Jan. 1995-Dec. 1995, Jan. 1994-May 1994," Technology Transfer Information Center, National Agricultural Library, United States Department of Agriculture, at http://www.nal.usda.gov/ttic/biofuels/hicks.htm (last visited Mar. 17, 2003).
Ostlund, Jr., R.E., et al., "Phytosterols that are naturally present in commercial corn oil significantly reduce cholesterol absorption in humans," *Am. J. Clin. Nutr.* 75:1000-1004, American Society for Clinical Nutrition (Jun. 2002).
PubMed abstract for Popov, A., et al., "[Free and bound sterol content of sunflower, soy bean and maize oils]," *Nahrung* 19:547-549, Weinheim VCH (1975), abstract only.
Singh, V., et al., "Effect of Various Acids and Sulfites in Steep Solution on Yields and Composition of Corn Fiber and Corn Fiber Oil," *Cereal Chem.* 77:665-668, American Association of Cereal Chemists (2000).
"12 Principles of Green Chemistry," The Website of the American Chemical Society (2003), at http://www.chemistry.org/portal/a/c/s/1/acsdisplay.html?DOC=education\greenchem\principles.html.

* cited by examiner

*Primary Examiner*—Michele Flood
(74) *Attorney, Agent, or Firm*—Kirkpatrick & Lockhart Preston Gates Ellis LLP

(57) ABSTRACT

The present invention relates to the use of "green" or relatively benign solvents such as ethanol, ethanol/water, isopropyl alcohol, isopropyl alcohol/water, ethyl lactate, acetone, butanol, isoamyl alcohol, or ethyl acetate to extract phytosterols from wet corn fiber. The resulting oil product contains free phytosterols and free fatty acids.

29 Claims, 1 Drawing Sheet

EXTRACTION OF PHYTOSTEROLS FROM CORN FIBER USING GREEN SOLVENTS

CROSS-REFERENCE TO RELATED APPLICATION

This application claims the benefit of U.S. Provisional Application No. 60/365,816, filed Mar. 21, 2002, the content of which is incorporated herein by reference.

BACKGROUND OF THE INVENTION

1. Field of the Invention

The present invention relates to the use of "green" or relatively benign solvents such as ethanol, ethanol/water, isopropyl alcohol, isopropyl alcohol/water, ethyl lactate, acetone, butanol, isoamyl alcohol, or ethyl acetate to extract phytosterols from wet corn fiber.

2. Background Art

Cholesterol is an important part of every human's daily diet because it is needed in the body for certain important functions, such as forming nerve cell membranes and aiding the production of hormones. Normally, cholesterol is absorbed in the small intestine and is eventually carried by special lipid and protein complexes called Low Density Lipoproteins ("LDL"). LDL delivers cholesterol to the tissues via the blood and cells that need cholesterol express specific, external LDL receptors. High Density Lipoproteins ("HDL") collect cholesterol from dying cells and membranes undergoing turnover for recycling. The ratio between LDL and HDL in the bloodstream can be used to predict a patient's health status. If the ratio is above 3.5, then the patient has an elevated LDL or blood cholesterol level. (Biochemistry, 5th Edition, Berg, J. M., et al., eds., W. H. Freeman & Co, New York, N.Y., pp. 726-731 (2002)).

The amount of cholesterol necessary to carry out these functions is, unfortunately, only a tiny portion of the daily cholesterol intake of an average American. When excess cholesterol is ingested or when there is a breakdown in the processing of cholesterol from LDL, it can lead to artherosclerosis or clogged arteries. If an artery to the heart is blocked by an artherosclerotic plaque, it can cause a heart attack. Similiar blockage of arteries in the brain can lead to strokes. To lower the risk of a patient having a heart attack or stroke, the blood cholesterol level must be lowered (WO 01/15552). The most direct route to manage blood cholesterol is by lowering dietary intake. There are only a few drugs on the market that inhibit bile recycling or de novo cholesterol biosynthesis (<<http://nh1bisupport.com/chd1/meds.htm>>, National Heart, Lung, and Blood Institute, (2002)).

Phytosterols, or plant fats that include beta-sitosterol and its glucoside beta-sitosterolin, closely resemble the molecule cholesterol (Hicks and Moreau, *Food Technology* 55(1):63-67 (2001)). Since the mid-1960's, over 5,000 research articles have been published on the positive benefits of phytosterols, including the fact that they interfere with cholesterol absorption. The lowered absorption of cholesterol from the intestines decreases the LDL, lowering plasma cholesterol levels (Nigon, et al., *Sang Thrombose Vaisseaux* 12(8):483-490 (2000)).

Phytosterols have been found to be present in corn fiber, which is a by-product obtained from "wet-milling" corn (Moreau, et al., *Biochemical Society Transactions* 28(6): 803-806 (2000)). "Wet-milling" is a process by which corn can be separated into its basic components: starch, protein, oil, and fiber (<http://www.corn.org/web/process.htm>, Corn Refiners Association, (2002)).

"Corn fiber" is defined in U.S. Pat. No. 5,843,499 as "the product obtained from the wet-milling process, which involves an initial steeping of corn kernels in aqueous sulfur dioxide at an elevated temperature followed by gentle grinding and physical separation of the outer fiber layers from starch, protein and other components" (see also Singh, et al, *Cereal Chem.* 77(5):665-668 (2000)). For the purpose of this invention, corn fiber will have the meaning just described.

Corn fiber is produced by corn wet-milling at the rate of ~11% per bushel of corn processed. This means that over 14,000 tons of corn gluten feed and corn oil meal are produced per day, with corn oil meal being a very small fraction (less than 680 tons per day) (<<http://corn.org/web/shipprod.htm>>, Corn Refiners Association, (2003)). Currently, corn fiber is a low value waste stream that, with the addition of protein, can be sold as corn gluten (animal) feed (U.S. Pat. No. 4,038,481). In an effort to upgrade this co-product and harvest phytosterols, a cost-effective strategy was developed. To this end, a solvent system compatible with current corn wet-milling operations is important.

According to Moreau et al. oils containing phytosterols can be extracted from corn fiber using hexanes with the antioxidant BHT present. The Moreau procedures were completed on dried, ground corn fiber at room temperature with agitation. This extraction resulted in mixed oils containing triglycerides (TAG), fatty acid esters of phytosterols (St-FA), free fatty acids (FFA), tocopherols, free phytosterols (St), and ferulic acid esters of phytosterols (St-F). Moreau reported approximately 15% (wt/wt) sterol content with about 7% as St-FA (U.S. Pat. No. 5,843,499).

Moreau's method differs significantly from the present invention in that the extractions described herein may be carried out on either dry corn fiber or wet, unground corn fiber. An advantage to the present invention is that the corn fiber need not be dried or ground. While some reduction of water may be necessary, the lack of need for completely dry corn fiber is an advantage because the energy needed to reduce the fiber from 65% water (typical for wet-milled corn fiber) to 0% water is high. Additionally, grain dust explosions are a huge potential hazard for grain storage and milling operations. This hazard is greatly reduced by not grinding the corn fiber to the 20 mesh grind that the '499 patent suggests. By processing wet corn fiber with larger particle sizes the chance of a grain dust explosion is minimized.

The present invention also differs from the process outlined in the '499 patent because the phytosterols isolated using the method of the present invention are isolated as free sterols, not as a mixture of steryl ferulates, steryl fatty acid esters, and free sterols as seen by Moreau. The present invention provides for both the selective and total extraction of phytosterols based upon the extraction solvent and water content. The saponification conditions applied in the present invention are effective at reducing the oil to two major components: free fatty acids and free sterols.

One goal of the present invention was to optimize a cost-effective method of selectively extracting phytosterols from corn fiber using an environmentally friendly solvent, which is an improvement on the current technology. Green solvents are less toxic than common organic solvents, like hexane (Hanmaoungjai, P., et al., *J. Am. Oil Chem. Soc.* 78(8):817-821 (2001)). The term "green solvents" in the present disclosure will be considered to comprise water, ethanol, isopropyl alcohol, ethyl lactate, acetone, butanol, isoamyl alcohol, or ethyl acetate and a blend of one or more thereof. These solvents degrade more rapidly in the environment, are less toxic to mammals than many other solvents, and are consistent with the twelve principles of "green chemistry" (<<http://chemistry.org/portal/Chemistry?PID=acsdisplay.html&DOC=education\greenchem\principles.html>>, The American Chemical Society, (2002)).

Ethanol and ethanol/water mixtures are most compatible with current corn wet-milling plants since both ethanol and water are available for use in such plants. The inventors of the present invention have found that pure ethanol extracts have the same yield of corn fiber oil as if extracted by hexane.

Organic solvents do not selectively extract only phytosterols, which is in contrast to the solvents used in the present invention. It is a common known practice to those skilled in the art that extraction of phytosterols can be done by reacting dried, ground corn fiber with organic solvents, such as hexane, chloroform, ether, and methanol. However, these organic solvents extract a mixture of components from the corn fiber, including triglycerides, and therefore the final isolation of the phytosterols from the triglycerides and further purification by crystallization is further complicated.

Purifying a corn lipid extract using crystallization is disclosed in U.S. Pat. No. 6,352,845. The '845 patent discloses an extraction of a corn fiber lipid fraction from wet or dry unground corn fiber using a solvent. After the solvent is removed from the corn fiber lipid fraction, phytosterols and phytosterol esters can be isolated from the corn fiber lipid fraction in a mixture or as individual fractions by crystallization.

WO 00/69280 teaches using ethanol (a green solvent) to extract total oil and zein (protein) from dry-milled corn residue (or corn bran). This is different from the present invention because the starting material for 00/69280 is corn bran, which is a byproduct of dry milling, rather than corn fiber, which is derived from corn wet milling. Corn fiber is a better source of phytosterols than corn bran because corn fiber contains less oil and has a higher phytosterol content. The present invention has optimized the method of selectively extracting the total sterols from corn without any triglycerides or proteins in the final oil product. The wet corn fiber used in the present invention can be taken directly from a wet mill and reacted with a green solvent to start the present disclosed invention.

SUMMARY OF THE INVENTION

The present invention relates to extracting phytosterols from corn fiber using an environmentally friendly solvent, wherein the corn fiber need not be dried or ground. The present invention has optimized the method of selectively extracting the total sterols from corn fiber without any triglycerides or proteins in the final oil product. The wet corn fiber used in the present invention can be taken directly from a wet mill and reacted with a green solvent to start the present disclosed invention.

The solvents to be used in the present invention can be selected from the group of green solvents comprising water, ethanol, isopropyl alcohol, ethyl lactate, acetone, butanol, isoamyl alcohol, ethyl acetate and a blend of one or more thereof. Most experiments disclosed herein were completed with a mixture of ethanol and water. Many ratios of ethanol to water were evaluated as to the effectiveness of extracting the phytosterols. In a preferred embodiment, the ratio of ethanol to water is 80% ethanol/20% water.

In another preferred embodiment, the corn fiber and solvent mixture is agitated and heated. After agitating and heating the mixture, the solid particles were removed by filtration.

In most cases, direct treatment with base (10% or 1% NaOH or KOH) degraded any triglycerides, steryl fatty acid esters, and/or steryl ferulate esters that were extracted. Heating enhanced the reaction rate for saponification and created free fatty acids, fatty acid esters, free sterols, free stanols, and other small molecules (like ferulic acid).

In one embodiment, the supernatant of this filtration was distilled to remove the majority of the solvent by simple, vacuum distillation. The water-soluble components of the resulting mixture were removed after saponification (base treatment) by extracting twice with hexane. The remainder of the water was then removed by drying with $MgSO_4$ and the hexane was removed by simple, vacuum distillation. This resulted in a final, phytosterol-rich oil.

One goal of the present invention was to optimize a cost-effective method of selectively extracting phytosterols from corn fiber using an environmentally friendly solvent, which is an improvement on the current technology. Another advantage to the present invention is that the corn fiber need not be dried or ground. The present invention has optimized the method of selectively extracting the total sterols from corn without any triglycerides or proteins in the final oil product.

The wet corn fiber used in the present invention can be taken directly from a wet mill and reacted with a green solvent to start the present disclosed invention. The use of wet-milled corn fiber aids process integration with an existing wet mill operation by reducing the number of steps required to obtain the phytosterols and saving the energy that is normally required to dry the corn fiber (Corn: Chemistry and Technology, Watson, S. A. et al., eds., American Association of Cereal Chemicals, Inc., St. Paul, Minn., p.384 (1987)). Additional savings are also realized because of the reduced energy required for the defatted fiber. Less drying is required for the post-solvent treatment after treating the corn fiber with a solvent. This is due to the fact that the extraction aids in significant water removal. In the currently existing wet mills, the corn fiber stream that results from the process according to the present invention can be combined with evaporated steepwater, and then dried and sold as corn gluten feed. An advantage of the present invention is that whether the water originates from wet fiber or added to dry fiber with the solvent, as in one embodiment using an ethanol/water mixture, the results of the extraction are the same.

DETAILED DESCRIPTION OF THE INVENTION

Figure 1:
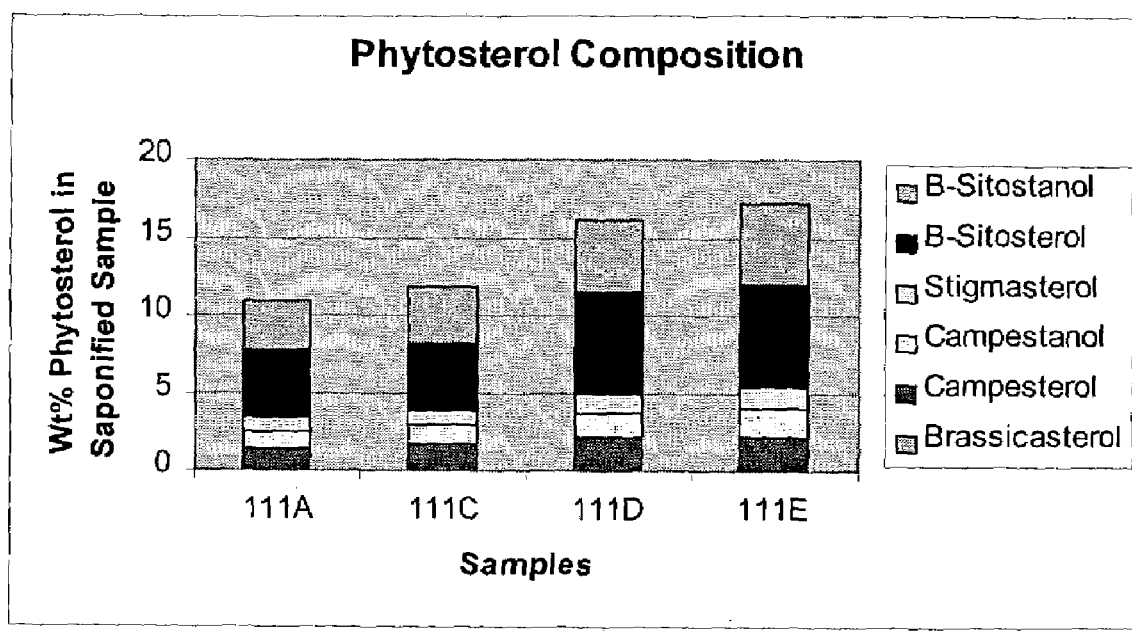
FIG. 1 shows the sterol compositions for Samples 111A-4195, 111C-4195, 111D-4195, and 111E-4195.

In the present invention, it was determined that when green solvents are mixed with corn fiber, sterols can be selectively extracted without extracting any triglycerides. It was determined that this could be done with native or destarched corn fiber. Accordingly, both native and destarched corn fiber can be used in the present invention. For the purpose of this disclosure, "native corn fiber" will be considered as corn fiber that was taken directly from the corn wet-milling process and, without further manipulation, was used as starting material for the present invention. "Destarched corn fiber" is corn fiber that has been taken directly from the corn wet-milling process and was enzymatically destarched. It was found that destarching the corn fiber before beginning the process as described in the present invention resulted in a final oil with a higher percentage of total sterols.

For the purposes of the present invention, "phytosterols" will be assumed to include beta-sitosterol, sitostanol, campesterol, campestanol, stigmasterol, stigmastanol, brassicasterol, and other compounds containing the sterol ring system. In this disclosure, "total sterols" includes all of the phytosterols described above. Phytosterols will also be assumed to include sterol glucosides, sterol fatty acid esters, and sterol ferulate esters.

As mentioned above, the green solvent to be used in the present invention can be, for example, water, ethanol, isopropyl alcohol, ethyl lactate, acetone, butanol, isoamyl alcohol, ethyl acetate or a blend of one or more thereof. Most experiments of the present invention were done with a mixture of ethanol and water rather than only ethanol for economic reasons. Wet corn fiber directly from the wet-milling process is approximately 65% water. The method was successfully carried out using corn fiber directly from the wet milling process; however, the disadvantage of having corn fiber with 65% water was that to achieve an 80% ethanol/20% water mixture, an extreme amount of anhydrous ethanol had to be added. The method was optimized by first removing some of this water from the corn fiber by vacuum drying at 80° C. The water was removed until the corn fiber was ~20% water. This made the volumes necessary to achieve the 80/20 ratio of ethanol to water more manageable. Many other ratios of ethanol to water were attempted successfully and are within the scope of the present invention; 80/20 gave the best results in terms of selectively extracting phytosterols. The use of wet corn fiber is an important concept because it aids in improved corn wet milling process economics by integration into existing wet mills with the minimum number of steps. The removal of complete drying results in energy cost savings, which makes the process of phytosterol extraction more economically attractive.

In the present invention, it was determined that agitating the destarched, wet corn fiber and ethanol mixture was preferred for isolation of the phytosterols. The method was completed without agitating and phytosterols were selectively extracted. However, the percentage of total sterols in the final oil without agitation was much lower than when agitation was utilized. Once it was determined that agitation was beneficial, the degree of agitation was optimized. The method was tested with up to 1000 revolutions per minute (rpm) of agitation. In a preferred embodiment, the mixture is agitated at 500 rpm.

Heating the mixture of wet corn fiber and ethanol was also utilized to optimize the amount of total sterols extracted. The mixture was heated with temperatures ranging from 25-50° C. In a preferred embodiment, the mixture is heated to a temperature of 50° C.

After agitating and heating the mixture, the solid particles can be removed. Filtration methods, which would be apparent to those skilled in the art include, but are not limited to, centrifugation, screw press, twin roll press and vacuum filtration with a porous screen.

Base-catalyzed saponification degraded any triglycerides, steryl fatty acid esters, and/or steryl ferulate esters that were extracted. Heating to 50° C. enhanced the reaction rate and created free fatty acids, fatty acid esters, free sterols, free stanols, and other small molecules (like ferulic acid). Sodium hydroxide and potassium hydroxide (1-10% wt/v) were explored. The results favor the use of 1% sodium hydroxide or caustic due to the minimum formation of salt (ash). The use of 1% NaOH also appears to aid the maximum removal of other co-extractants, such as diferuloylputrescine and coumaroylferuloylputrescine (Moreau et al., *Lipids* 36(8):839-844 (2001)).

The pH 2-4 product mixture was distilled to remove the majority of the ethanol. The inventors of the present invention attempted rotary evaporation, simple distillation and simple, vacuum distillation with the latter of the three being the preferred method. The supernatant was distilled to remove the ethanol, leaving anywhere from ⅓ to ¼ of the initial volume, with ¼ being preferred.

In one embodiment, the water-soluble components of the above resulting mixture are removed by treating the mixture with two times the above resulting volume of hexane. The hexane was dried with $MgSO_4$, then removed. Again, rotary evaporation, simple distillation and simple, vacuum distillation were all attempted. Simple, vacuum distillation was the preferred method. The final product was a phytosterol-rich oil.

EXAMPLES

Example 1

Solvent Study

This study compared solvents for selective extraction of phytosterols from corn fiber and was monitored by thin layer chromatography (TLC) using 95:5:1 (v/v/v) hexanes:isopropanol:acetic acid on silica gel with an acidic ferric chloride dip that, after heating, assists in visually detecting sterols and other lipid components. Sterols (St), steryl ferulates (St-F) and sterol fatty acid esters (St-FA) have a 0.1 mg detection limit, while the detection limit for free fatty acids (FFA) is 100 mg in this methodology.

Dry, ground, destarched corn fiber (DCF; ~4 g) was placed in six glass screwcap tubes. The solvent (40 mL) indicated in Table 1 was placed in the tube with the DCF. The tubes were incubated at 25° C. for 1 hour and 42° C. for 1 hour with agitation (200 rpm). Extracts were removed by filtration and the solvent was evaporated under reduced pressure. TLC was completed on these samples with standards present on the same plate.

TABLE 1

A preliminary study of the relationship between solvent and extractable lipid components in destarched corn fiber.

| Sample | Solvent | % Water | TLC Observations (most abundant to least abundant lipids) |
|---|---|---|---|
| 18A-4195 | Ethanol | 25 | FFA, St, St-F, TAG |
| 18B-4195 | Ethanol | 10 | FFA, St, St-F, TAG |
| 18C-4195 | Isopropanol | 10 | TAG, FFA, St, St-F, St-FA |
| 18D-4195 | Hexanes | 0 | TAG, FFA, St, St-F, St-FA |
| 18E-4195 | Ethyl Acetate | 0 | TAG, FFA, St, St-F, St-FA |
| 18F-4195 | Ethanol | 0 | TAG, FFA, St, St-F, St-FA |

The typical composition of corn fiber oil is approximately 80 wt % triglycerides (TAG), yet the TLC data indicate that when ethanol/water was used as the solvent for extraction this was not the case. This study demonstrated that ethanol/ water mixtures did not extract the same lipid components in the same quantitative distribution as other solvents such as hexanes and ethyl acetate.

Example 2

Ethanol/Water Selectivity Study

This experiment was designed to investigate phytosterol extraction using different concentrations of water in ethanol.

Dry, ground, DCF (~8 g) was placed in Erlenmeyer flasks with 80 mL of ethanol/water. Each flask had a different ethanol/water mixture. The samples were immersed in the extractant for 2 hours at 25° C. and were extracted at 42° C. for two additional hours without agitation. The samples were filtered, and the solvent was removed by vacuum distillation, and desiccated. The lipid contents of these samples are described in Tables 2 and 3.

TABLE 2

A preliminary study of the relationship between water content and the ethanol extractable lipid components in DCF.

| Sample | Solvent | % Water | TLC Observations (most abundant to least abundant lipids) |
|---|---|---|---|
| 80A-4195 | Ethanol | 5 | TAG, FFA, St, St-F, St-FA |
| 80B-4195 | Ethanol | 10 | TAG, FFA, St, St-F, St-FA |
| 80C-4195 | Ethanol | 15 | TAG, FFA, St, St-F, St-FA |
| 80D-4195 | Ethanol | 20 | FFA, St, St-F, TAG |
| 80E-4195 | Ethanol | 25 | FFA, St, St-F |

These samples (80A-4195 through 80E-4195) contained significant nonlipid impurities as evidenced by large losses (~65%) during saponification reactions, making complete mass balance particularly challenging. These findings confirmed a recent paper by Moreau in *Lipids* that reports ethanol solvents will extract putrescine diesters as well as other nonlipid materials (Moreau, Robert A., et al., *Lipids* 36:839-844 (2001)). Reported in Table 3 are the total FFA and total St for each saponified sample. During saponification all St-FA and St-F were converted into St, and TAG was converted, predominantly, into FFAs.

TABLE 3

GC results for saponified, silylated DCF extracts obtained using different ethanol/water concentrations.

| Sample | % Water in ethanol | Total FFA, wt % | Total Sterols, wt % |
|---|---|---|---|
| 80A-4195 | 5 | 63 | 8 |
| 80B-4195 | 10 | 32 | 8 |
| 80C-4195 | 15 | 39 | 13 |
| 80D-4195 | 20 | 24 | 10 |
| 80E-4195 | 25 | 4 | 7 |

Both the total sterol content and the total free fatty acid content of the extract were impacted by the amount of water present in the ethanol. With only 5% water in ethanol, the FFA number is high and the sterol number was low, whereas with 15-20% water, sterols made up a little more than 10% of the sample. The lower the water content in ethanol, the more it extracted the same lipid components as hexane. There also appeared to be a solvent polarity range that is selective for sterols, since the peak sterol concentration is near 85% ethanol and 15% water.

Wet DCF (100 g; 64% water) was extracted with ethanol/water (600 mL) at 47° C. for two hours. The fiber was filtered while hot and the extract was subjected to solvent reduction via vacuum distillation followed by hexane/salt-water extraction. The hexane layer was dried with magnesium sulfate, filtered, and then distilled to crude lipids.

Tables 4 and 5 contain the results of both TLC and gas chromatography (GC) for Samples 111A-4195, 111C-4195, 111D-4195, and 111E-4195. At and above 15% water, the initial lipid extracts indicate selectivity toward FFA and away from TAG, thus enhancing the sterol content of the extracts. These results are similar to the selectivity observed when dry, ground DCF was used (see Tables 2 and 3). The sterol content of the final saponified oils were 15% and 17% when the extractant used initially was 20% and 25% water, respectively.

TABLE 4

A preliminary study of the relationship between water content and the ethanol-extractable components in DCF on a 100 g scale.

| Sample | % Water in ethanol | Wt % of saponified sample | TLC Observations (most abundant to least abundant lipids) |
|---|---|---|---|
| 111A-4195 | 5 | 0.8 | TAG, FFA, St, St-F, St-FA |
| 111C-4195 | 15 | 0.8 | FFA, TAG, St, St-F, St-FA |
| 111D-4195 | 20 | 0.4 | FFA, TAG, St, St-F, St-FA |
| 111E-4195 | 25 | 0.4 | FFA, St, ST-F, TAG, St-FA |

TABLE 5

GC results for saponified, silylated DCF extracts obtained using different ratios of ethanol/water.

| Sample | % Water in ethanol | Total FFA, wt % | Total Sterols, wt % |
|---|---|---|---|
| 111A-4195 | 5 | 48 | 11 |
| 111C-4195 | 15 | 46 | 12 |
| 111D-4195 | 20 | 48 | 15 |
| 111E-4195 | 25 | 30 | 17 |

Example 3

Agitated Batch Extraction of DCF with Ethanol/Water

Since the DCF is not ground, extraction efficiency was lower than anticipated for complete corn fiber oil extraction. Agitation is one way to increase extraction efficiency. For this series of pilot-scale experiments, a Microferm fermentor was used.

A. Using 80/20 Ethanol/Water

Sample #37-4233AR was prepared by extracting 750 g of dry DCF at 50° C. with 80/20 ethanol/water by stirring (500 rpm) in a Microferm fermentor for two hours. The material was vacuum filtered while hot to remove the solids. The extract was saponified using 10% wt/v KOH for two hours at 50° C. The saponification reaction was quenched with concentrated HCl to ~pH1 and the volume was reduced by simple vacuum distillation. Hexane extraction of the concentrated extract left many of the impurities behind resulting in a 2.1% wt sample/wt of original DCF, but only a 24% recovery of material after saponification. Sample #37-4233AR contained 60 wt % free fatty acids and 20 wt % total sterols. Despite an excess of base that generated salt upon quenching, the ash content was only 0.3% wt/wt. The water from the saponification step for Sample #37-4233AR was found to be low in amino acids, carbohydrates, and lipids.

A second 80/20 ethanol/water extraction resulted in Sample #93-4233AR. Dry, unground DCF (1000.0 g) was placed in the microferm fermentor and covered with 10.0 L of 80/20 Ethanol/water at 50° C. for 2 hours with agitation (1000 rpm). The solid material was filtered using cheesecloth, and the filtrate (5.8 L) was cooled to room temperature. The filtrate was saponified using 1% wt/v NaOH at 50° C. for 2 hours with 500 rpm agitation before quenching to pH 4.0 with phosphoric acid. The ethanol was removed with vacuum distillation to a volume of ~1.8 L. Extraction with hexanes (2 L), drying with magnesium sulfate, and distillation of the solvent resulted in Sample #93-4233AR (6.09 g; 0.6% wt sample/wt DCF). Total sterols for Sample #93-4233AR was 16.31 wt %. This number is only slightly lower than that found in Sample #37-4233AR. The results suggest that 1% base during saponification, as was used to prepare Sample #93-4233AR, is nearly as effective at saponification as was the 10% base utilized in preparing Sample #37-4233AR.

B. Using 95/5 Ethanol/Water.

DCF (750.7 g dry) was extracted with 95% ethanol for 2 hours at 50° C. in the Microferm Fermentor with agitation. Vacuum filtration recovered 6.4 L and resulted in a loss of 10.2% of the dry DCF mass. The volume of the extract was reduced to 2.15 L and aliquots were utilized in a variety of subsequent experiments.

Sample 50A-4233AR resulted from 300 mL of the extract being extracted with hexanes. The hexane layer was back-extracted with both 1M NaOH and 20% (v/v) $H_2SO_4$ to remove nonlipid impurities. The hexane layer was dried using $MgSO_4$ and the solvent removed using simple vacuum distillation. The mass of the resulting sample was 2.36 g and it contained 5.95 wt % total sterol despite not undergoing saponification prior to analysis. Approximately 75% of the total sample expected (14% by weight after saponification of the theoretical 3% oil from the starting DCF=3.14 g) was recovered in a single, hot extraction with ethanol/water. The 95/5 extract, with only acid and base washes, had a minimum of 6 wt % free sterol, since higher wt % sterols were possible via the degradation of fatty acid and ferulate esters.

Sample 60-4233AR resulted from 720 mL of the extract being refluxed for 2 hours with 1% (wt/v) KOH. The reaction was quenched to pH~1.5 and extracted with hexanes. The hexane layer was dried using $MgSO_4$ and the solvent removed using simple vacuum distillation. The semi-crystalline sample mass was 0.52 g, a mere 7% of the theoretical oil expectation. This low overall yield was consistent with a large loss of nonlipid material that becomes water soluble during treatment with base. Sample 60-4233AR contains 55 wt % total sterol.

C. Exploring Milder Saponification Conditions

The experiments were begun with 95% ethanol/5% water extract of DCF (1130 mL of 50-4233AR) which should result in ~0.8 g of saponified oil. Sodium hydroxide (1.3 g; 0.1 wt %) was added and the whole reaction mixture was transferred into the Parr Reactor. After 15 minutes of rapid bubbling of nitrogen gas, a 100 psi head pressure was initiated. Heating to 245° C. began and was maintained for an hour. It was necessary to periodically release pressure from the reactor in order to keep it below 1000 psi. The reactor was cooled using 25° C. water and disassembled in the hood. The contents were transferred to a 2 L Erlenmeyer flask and the reactor was rinsed with new ethanol (2×50 mL). The pH was adjusted using 85% phosphoric acid to ~6.9. A slight precipitate formed prior to ethanol removal by distillation. The reduced volume was extracted with hexanes. The hexane layer was dried with magnesium sulfate, filtered, and distilled to produce Sample 88-4233AR. Analysis of the product indicated 12.9% total sterols and 35% free fatty acids. TLC verified that there are both St-FA and TAG present in the sample that are part of the complete mass balance. No St-F ester could be detected by TLC, despite what appears to be an incomplete reaction. It also appeared that the low base, high temperature and pressure reaction was not as effective at degrading nonlipid material as 1% base at 50° C. for two hours.

Example 4

Using 1% Base During the Extraction Process

Dry DCF that had been partially de-oiled using 95/5 ethanol/water (50CF-4233AR; 100.2 g) was suspended in water (650 mL) and ethanol (100 mL) in the presence of 1% (wt/v) KOH. The mixture was boiled on a hot plate for two hours. After limited cooling and the addition of cool water (200 mL), ethanol (3 L to form 75/25 ethanol/water) was added to precipitate the solubilized carbohydrates. Vacuum filtration resulted in recovery of 3.4 L of solvent. The fiber was re-dried and found to have lost 16.2% (wt/wt) during the extraction. The filtrate was acidified to pH 2 and extracted once with equal volumes of hexanes. The hexane layer was dried using $MgSO_4$ and the solvent removed using simple vacuum distillation to produce the semi-crystalline Sample 64-4233AR. Sample 64-4233AR (1.54 g; 1.54 wt % based on deoiled DCF) contained 7.75 wt % total sterol and reinforces the fact that a single, batch extraction of DCF results in incomplete phytosterol extraction. Sample 64H2O-4233AR, the water layer, contained 2.0 wt % ferulic acid and about 10% less of coumaric acid. The total elemental phosphorus in Sample 64H2O-4233AR was 14 ppm.

Example 5

Extraction of Pretreated DCF Acid and Thermochemically Pre-treated CF

Drying of a sample of corn fiber that was pretreated by heating at 130° C. for 30 minutes in the presence of 0.8 wt % acid (to remove all the starch and hemicellulose) resulted in a mass of 81.54 g. The whole portion was extracted with 95% ethanol (650 mL) for 2 hours at 50° C. with gentle agitation. The fiber was removed by hot vacuum filtration. The residue was re-dried and found to be 14% lighter than the initial dry mass. Base (6.3 g NaOH) was added to the filtrate and the resulting solution was incubated at reflux for 2 hours. Quenching with sulfuric acid to pH~2 was followed by hexane extraction. The hexane layer was back-extracted with distilled water to ensure removal of the salts and dried with magnesium sulfate overnight. When the hexanes were removed, Sample 70-4233AR accounted for 7.08 g or 8.7% wt sample/wt of the starting thermochemically treated corn fiber. The combined water layers, Sample 70H2O-4233AR, contained 19 ppm elemental phosphorus and a total of 0.4 wt % ferulic acid. Coumaric acid was present at 47 ppm. Sample 70-4233AR had 6.13 wt % total sterols. These results suggest that removal of starch and hemicellulose reduce the ferulic acid content significantly, but appear to have a negligible impact on the phytosterol content of ethanol-extractable, saponified material.

Summary of Results from Examples 1-5

Table 6 details the conditions and results of the larger scale extractions. The range of phytosterol content is 6-55 wt % in the final oil samples. The only sample reported below that was not saponified was Sample 50A. Sample 50A came from the same initial corn fiber extract as both Sample 60-4233AR and Sample 88-4233AR. With 6 wt % for 50A, 13 wt % for 88, and 55 wt % for 60, it appears that the saponification conditions can make a significant difference in the final oil. The optimal saponification appears to occur with 1% base. When the extraction solvent is 20% water in ethanol (samples 37 and 90) the variation in sterol content of the final, saponified oil is not as dramatic. This is due to the fact that the farther the water content in the extractant is from 0%, the less sterol fatty acid esters are removed from the corn fiber.

Corn fiber that has been pretreated by initial oil removal (i.e., Sample 64) or by thermochemical (i.e., Sample 70) do not show significant differences in the sterol content of the final, saponified oil. The sterol content of Samples 64 (7.75 wt %) and 70 (6.13 wt %) is similar to the unsaponified extract 50A (5.95 wt %).

TABLE 6

Compilation of extraction and saponification conditions with results from Examples 1-5.

| Sample | % Water in Ethanol extraction | Saponification Conditions | Yield (Wt % sample/fiber) | Sterol Content (Wt % sample/oil) | FFA Content (Wt % sample/oil) |
|---|---|---|---|---|---|
| 37-4233AR | 20 | 10% base; 2 hrs | 0.5 | 20 | 60 |
| 93-4233AR | 20 | 1% base; 2 hrs | 0.6 | 16.31 | 57.67 |
| 50-4233AR | 5 | None; washed extract with acid & base | 2.25 | 5.95 | 0.83 |
| 60-4233AR | 5 | 1% base; 2 hrs | 0.21 | 55 | 9.2 |
| 88-4233AR | 5 | 0.1% base; 250 C.; 1000 psi; 1 hr | — | 12.9 | 35 |
| 64-4233AR | 25 with 1% base; deoiled DCF | During extraction; 2 hrs | 1.54 | 7.75 | 27.4 |
| 70-4233AR | 5; acid & thermo. DCF | 10% base; 2 hrs | 8.7 | 6.13 | 73.5 |

Having now fully described the present invention in some detail for purposes of clarity of understanding, it will be obvious to one of ordinary skill in the art that the same can performed by modifying or changing the invention within a wide and equivalent range of conditions, formulations, and other parameters without affecting the scope of the invention or any specific embodiment thereof, and that such modifications or changes are intended to be encompassed within the scope of the appended claims.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

What is claimed is:

1. A method of extracting phytosterols from corn fiber comprising:
    a) combining corn fiber having one or more phytosterols with a green solvent selected from the group consisting of water, ethanol, isopropyl alcohol, ethyl lactate, acetone, butanol, isoamyl alcohol, ethyl acetate, and any combinations thereof to produce a mixture comprising said green solvent and said corn fiber, wherein said mixture further comprises one or more dissolved phytosterols from said corn fiber;
    b) removing said corn fiber from said mixture of a) to produce an extract;
    c) saponifying said extract of b) to produce a saponified extract;
    d) removing said green solvent from said saponified extract of c) to produce a saponified material;
    e) combining said saponified material of d) with an organic solvent thereby extracting water soluble components from said saponified material of d);
    f) removing said organic solvent of e) from said saponified material of e); and
    g) recovering said saponified material of f) to obtain a composition comprising phytosterols.

2. The method of claim 1, wherein said composition consists essentially of free phytosterols and oil.

3. The method of claim 2, wherein said oil consists essentially of free fatty acids.

4. The method of claim 1, wherein said composition comprises phytosterols selected from the group consisting of beta-sitosterol, sitostanol, campesterol, campestanol, stigmasterol, stigmastanol, brassicasterol, sterol glucosides, sterol esters, sterol fatty acid esters, sterol ferulates, sterol ferulate esters, and combinations thereof.

5. The method of claim 1, wherein said corn fiber is prepared by wet-milling corn.

6. The method of claim 1, wherein said corn fiber is destarched.

7. The method of claim 5, wherein an amount of water is removed from said wet-milled corn fiber prior to the combining of said corn fiber with said green solvent.

8. The method of claim 7, wherein said corn fiber comprises up to about 65% water.

9. The method of claim 8, wherein said corn fiber comprises about 20% water.

10. The method of claim 1, wherein said green solvent consists of a mixture of water and ethanol.

11. The method of claim 10, wherein said green solvent consists of about 80% ethanol and about 20% water.

12. The method of claim 1, wherein agitation is performed on said mixture.

13. The method of claim 12, wherein said agitation is performed at a speed of up to 1000 rpm.

14. The method of claim 13, wherein said agitation is performed at a speed from 250 to 1000 rpm.

15. The method of claim 14, wherein said agitation is performed at a speed of about 500 rpm.

16. The method of claim 1, wherein heating is performed on said mixture.

17. The method of claim 16, wherein said heating occurs at a temperature from 25° C. to 50° C.

18. The method of claim 17, wherein said heating occurs at a temperature of 50° C.

19. The method of claim 1, wherein said saponifying is performed by adding an amount of base that is from 0.1% weight/volume to 10% weight/volume of said extract of b).

20. The method of claim 19, wherein said saponifying is performed by adding an amount of base that is about 1% weight/volume of said extract of b).

21. The method of claim 20, wherein said saponifying is performed at a temperature of about 250° C. and at a pressure of up to 1000 psi.

22. The method of claim 1, wherein said green solvent is removed from said saponified material of d) by simple distillation.

23. The method of claim 1, wherein said green solvent is removed from said saponified material of d) by rotary evaporation.

24. The method of claim 1, wherein said green solvent is removed from said saponified material of d) by simple vacuum distillation.

25. The method of claim 1, wherein said organic solvent is removed by simple distillation.

26. The method of claim 1, wherein said organic solvent is removed by rotary evaporation.

27. The method of claim 1, wherein said organic solvent is removed by simple vacuum distillation.

28. A phytosterol composition extracted by the method of claim 1.

29. The method of claim 1, wherein said organic solvent is hexane.

* * * * *